United States Patent [19]
Chattopadhyay et al.

[11] Patent Number: 6,028,206
[45] Date of Patent: Feb. 22, 2000

[54] PROCESS FOR THE PRODUCTION OF IMPORTANT TAXOL ANALOGUES 10-DEACETYL TAXOL A, B, AND C

[75] Inventors: Sunil Kumar Chattopadhyay; Ram Prakash Sharma; Sushil Kumar, all of Lucknow, India

[73] Assignee: Council of Scientific and Industrial Research, New Delhi, India

[21] Appl. No.: 09/264,383

[22] Filed: Mar. 5, 1999

[30] Foreign Application Priority Data

Feb. 12, 1999 [IN] India ................. 231/DEL/99

[51] Int. Cl.⁷ ......................................... C07D 305/14
[52] U.S. Cl. ................................. 549/510; 549/511
[58] Field of Search ......................... 549/510, 511

[56] References Cited

U.S. PATENT DOCUMENTS 5,367,086  11/1994  Rao ........................... 549/510

*Primary Examiner*—Ba K. Trinh
*Attorney, Agent, or Firm*—Ladas & Parry

[57] ABSTRACT

The present invention relates to an improved process for the production of important taxol analogues 10-deacetyl taxol A,B and C of the formula (2)

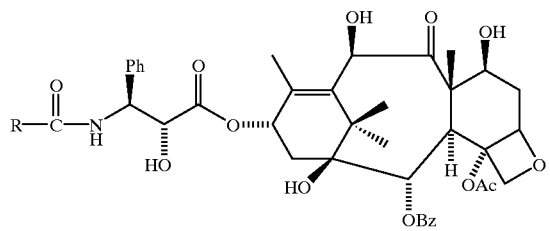

(2)

R=C$_6$H$_5$ (10 deacetyl taxol A)
=CH$_3$C═CHCH$_3$ (10-deacetyl taxol B)
=C$_5$H$_{11}$ (10-deacetyl taxol C)

where R represent C$_6$H$_5$ (10-deacetyl taxol A) or, CH$_3$C═CHCH$_3$ (10-deacetyl taxol B) or, C$_5$H$_{11}$ (10-deacetyl taxol C) which comprises (a) dissolving the taxol analogues 7-xylosyl-10-deacetyl taxol A,B,C of the formula (1)

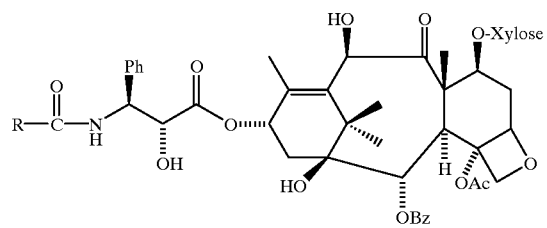

(1)

R=C$_6$H$_5$ (10 deacetyl taxol A)
=CH$_3$C═CHCH$_3$ (10-deacetyl taxol B)
=C$_5$H$_{11}$ (10-deacetyl taxol C)

where R represents C$_6$H$_5$ (taxol analogue A or xyloside A), or CH$_3$C═CHCH$_3$ (taxol analogue B or xyloside B) or C$_5$H$_{11}$ (taxol analogue C or xyloside C) in a polar solvent (b) reacting the resultant solution with periodate for 20–40 hours at 20–40° C. to cleave the diol system of the xyloside into dialdehyde, (c) treating the generated dialdehyde in a mixture of polar solvent-organic acid mixture with salts of amines at 0–40° C. for 12–18 hours and (d) isolating the 10-deacetyl taxol A,B,C by chromatography.

11 Claims, No Drawings

PROCESS FOR THE PRODUCTION OF IMPORTANT TAXOL ANALOGUES 10-DEACETYL TAXOL A, B, AND C

FIELD OF INVENTION

This invention relates to an improved process for the production of important taxol precursors 10-deacetyl taxol A, B and C. More particularly, this invention relates to a process for the conversion of taxol analogues 7-xylosyl-10-deacetyl taxols A, B and C of the formula (1)

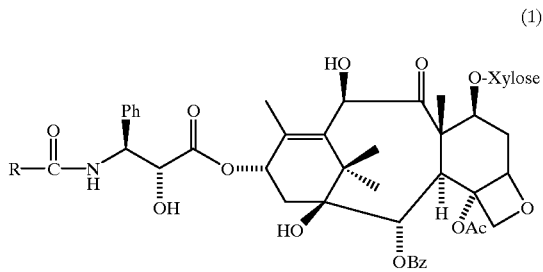

(1)

Where,

R=$C_6H_5$ (taxol analogue A)

=$CH_3C$=$CHCH_3$ (taxol analogue B)

=$C_5H_{11}$ (taxol analogue C)

represents $C_6H_5$ (taxol analogue A or xyloside A), OR, $CH_3C$=$CHCH_3$ (taxol analogue B or, xyloside B), or, $C_5H_{11}$ (taxol analogue C or, xyloside C) into 10-deacetyl taxols A,B,C (10-DAT-A,B,C). 10-deacetyl taxol A,B,C have the formula (2) where R=$C_6H_5$ (10-deacetyl taxol A), or $CH_3C$=$CHCH_3$ (10-deacetyl taxol B), or, $C_5H_{11}$ (19deacetyl taxol C)

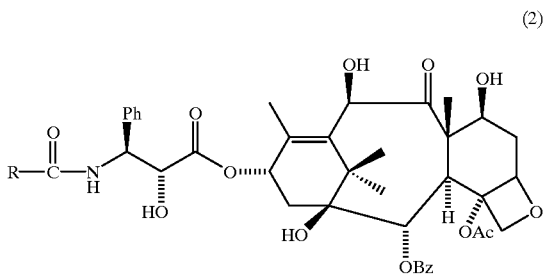

(2)

R=$C_6H_5$ (10 deacetyl taxol A)

=$CH_3C$=$CHCH_3$ (10-deacetyl taxol B)

=$C_5H_{11}$ (10-deacetyl taxol C)

BACKGROUND OF THE INVENTION

Taxols A and B are also known in the literature as taxol and cephalomannine and taxol C has no other name [Mise en evidence nouveaux analogues du taxol extracts de *Taxus baccata*. V.Senilh, S. Blechert, M. Colin, D. Guenard, F. Picot, P. Potier and P. Verenne, *Journal of Natural products* 47, 131–137 (1984)].

Out of the three taxols A,B,C, only taxol A(=taxol) is used clinically for the treatments of ovarian and breast cancers. Various types of cancers have been treated with taxol A and the results in the treatments of ovarian and breast cancers are very promising. Taxol A (=taxol) has been approved by the Food and Drug Administration (FDA) of the United States for the treatments of ovarian and breast cancers.

Taxol B (=cephalomannine) has been isolated from the leaves, stems, roots of *Taxus wallichiana*; It is not clinically used. [Antileukemic alkaloids from *Taxus wallichiana*. R. W. Miller, R. G. Powell, C. R. Smith, Jr., E. Arnold and J. Clardy, *Journal of organic Chemistry* 46, 1469–1474 (1981)].

Taxol C has been isolated from the roots of *Taxus media* [Taxol analogues from the roots of *Taxus media*. L. Barboni, P. Gariboldi, E. Torregiani, G. Appendino, B. Gabetta and E. Bombardelli, *Phytochemistry* 36, 987–990 (1994)]. Taxol C has also been isolated from the cell cultures of *Taxus baccata* and it showed potent and selective cytotoxicity against cell lines of non-small-cell lung cancer, small cell lung cancer, colon cancer, CNS cancer and ovarian cancer; [New bioactive taxoids from cell cultures of *Taxus baccata*. W. Ma, G. L. Park, G. A. Gomez, M. H. Nieder, T. I. Adams, J. S. Aynsley, O. P. Sahai, R. J. Smith, R. W. Stahlhut, P. J. Hylands, F. Bitsch and C. shackleton, *Journal of Natural Products* 57, 116–122 (1994)].

Taxol A, a highly oxygenated diterpenoid molecule and a potent anticancer drug was first isolated from the stem bark of *Taxus brevifolia*. Thereafter, it has also been isolated from other Taxus species including *Taxus wallichiana*. Taxol A, a structurally complicated and chemically labile molecule needed special and careful extraction and separation procedures for its isolation from plant materials. Unfortunately, most of works are proprietary in nature and have not been published. The American workers have used alcohol to extract taxol from the stem bark of *T. brevifolia* and isolation of taxol from the alcoholic extract used sequential column chromatography over silica with methanol-chloroform mixture (2:98) as the eluting solvent to yield a mixture of taxol A(=taxol) and Taxol B (cephalomannine). In one of the prior art process, Taxol A has been separated and isolated from the mixture containing taxol A and Taxol B with a yield of 0.01% either by repeated column chromatography over silica gel or by high performance liquid chromatography (HPLC). [M. C. Wani, H. I. Taylor, M. E. Wall, P. Coggan and A. T. Mc Phail. Plant antitumor agents VI: The isolation and structure of taxol, a novel antileukemic and antitumor agent from *Taxus brevifolia*, *Journal of the American Chemical Society* 93, 2325 (1971); and J. H. Cardellina: HPLC separation of taxol and cephalomannine, *Journal of liquid chromatography* 14, 659(1991)].

According to another prior art process, Taxol A has been isolated from the stem bark of *Taxus wallichiana* with a yield of 0.02%. The isolation process involves extracting the stem bark with methanol, partitioning of the methanolic extract between water and chloroform and isolation of taxol A from the chloroform soluble fraction by column chromatography over silica gel [S. K. Chattopadhyay, V. K. Tripathi, R. S. Thakur, R. P. Sharma and S. P. Jain. Isolation of taxol, 10-deacetyl baccatin III and (–) betuligenol from *Taxus Baccata Indian J. Chem.* 33B,409 (1994)]

10-deacetyl taxol A and C are important precursors as they can be converted into taxol A and C. Moreover, 10-deacetyl taxol A is the starting material for many newly developed analogues of taxol A. 10-DAT, A can be isolated with a yield of 0.0021% from the ethanolic extract of the roots, stems and needles of *T. wallichiana* by repeated column chromatography over silica gel followed by high pressure liquid chromatography [J. L. Mclaughlin, R. W. Miller, P. G. Powell and C. R. Smith, Jr. 19-hydroxy baccatin III, 10-deacetyl caphalomannine and 10-deacetyl taxol, new antitumor taxanes from *Taxus wallichiana*. *Journal of natural Products* 44,312–319 (1981)].

10-deacetyl taxol C has been isolated from the cell cultures of *Taxus baccata* with a yield of 0.0001%. [New bioactive taxoids from cell cultures of *Taxus baccata*. W. Ma, G. L. Park, G. A. Gomez, M. H. Nieder, T. I. Adams, J. S. Aynsley, O. P. Sahai, R. J. Smith, R. W. Stahlhut, P. J. Hylands, F. Bitsch and C. Shackleton, *Journal of Natural Products* 57,116–122 (1994)].

According to a prior art process, the taxol analogues 7-xylosyl-10-deacetyl taxols A,B,C of the formula (1) where R represents $C_6H_5$ (taxol analogue A), or $CH_3C=CHCH_3$ (taxolanalogue B) or, $C_5H_{11}$ (taxol analogue C) can be isolated from the stem bark of the Himalayan yew. *Taxus wallichiana* with higher yields in which no solvent partitioning has been used to isolate the analogues. The yields of 7-xylosyl-10-deacetyl taxols A,B and C obtained were 0.5, 0.02 and 0.0075% respectively. The process comprises extracting air dried pulverized plant materials with alcohols at room temperature, evaporating the solvent to obtain a residue, stirring the resultant residue with water to obtain a thick precipitate, isolating the analogues 7-xylosyl-10deacetyl-taxol A, 7-xylosyl-10-deacetyl taxol B, and 7-xylosyl-10-deacetyl taxol C from the precipitate by flash chromatography over a bed of silica gel [A process for the production of taxol. S. K. Chattopadhyay, R. P. Sharma, Sushil Kumar, K. P. Madhusudanan, Eurorean patent application No. 97306905.7-1521, Dec. 2, 1997].

According to a prior art process, taxol analogues 7-xylosyl-10-deacetyl taxol A and B have been converted into taxol A (=taxol) and taxol B (cephalomannine) by K. V. Rao [Process for the preparation of taxol and 10-deacetyl taxol, K. V. Rao, U.S. patent application Ser. No. 851,469, Mar. 13, 1992]. The process for the preparation of taxol A or B involved reacting the analogue 7-xylosyl-10-deacetyl taxol A or B with periodate in methanol, chloroform and sulphuric acid mixture at 20–60° C. to give a dialdehyde product which was then treated with phenylhydrazine in methanol-aqueous acid mixture and heated at 50–60° C. to degrade the dialdehyde into 10-deacetyl taxol A or B which was then isolated by column chromatography.

The process for preparation of the 10-deacetyl A or B as described by Rao suffers from disadvantages which include (a)—low yield of the 10-deacetyl taxol A or B, (b)—carrying out the periodate oxidation of the 7-xylosyl-10-deacetyl taxol A or B in presence of mineral acid (although it is mentioned by Rao in his patent application that periodate oxidation can also be carried out under neutral condition in presence of excess sodium bicarbonate, the presence of excess dissolved sodium carbonate may lead to degradation of the side chain from dialdehyde leading to a mixture of products, and (c) heating the periodate oxidation product with phenyl hydrazine in methanol-aqueous acetic acid mixture at 50–60° C. to degrade the periodate oxidation product into 10-deacetyl taxol A or B. Moreover, the process for the production of 10-deacetyl taxol C from the analogue 7-xylosyl-10-deacetyl taxol C has not been covered by Rao in his patent application.

According to another prior art process developed by Chattopadhyay et al, the 7-xylosyl-10-deacetyl taxols A, B and C can be converted into 10-deacetyl taxol A, B and C [A process for the production of taxol. S. K. Chattopadhyay, R. P. Sharma, Sushil Kumar and K. P. Madhusudanan, European Patent Application No. 97306905.7-1521, Dec. 2, 1997]. The process for the preparation of 10-deacetyl taxol A or B or C involved dissolving the analogue 7-xylosyl-10-deacetyl taxol A or B or C in a polar solvent, reaching the resultant solution with periodate to cleave the diol system of the xyloside into dialdehyde, reducing the dialdehyde solution in a mixture of polar solvent-acetic acid mixture with borohydride, acidifying the resultant acetal with mineral acid in a chlorinated solvent to yield 10-deacetyl taxol A or B or C.

Although the process developed by Chattopadhyay et al is superior to Rao process in terms of yield of 10-deacetyl taxol A or B or C, it has more steps to get the products.

SUMMARY OF THE INVENTION

In order to overcome the drawbacks of the prior art processes, we have developed an improved process as compared to our previous process for the production of 10-deacetyl taxols A, B and C. The improved process comprises—(1) dissolving the taxol analogue 7-xylosyl-10-deacetyl taxol A or B or C in a polar solvent and reacting with periodates at ambient temperature into dialdehyde, (2) treating the dialdehyde solution in a polar solvent organic acid mixture with salts of amine at 0–40° C. to give the 10-deacetyl taxol A or B or C followed by (3) purification by column chromatography.

DETAILED DESCRIPTION OF THE PROCESS

The object of the present invention is to develop an improved process for conversion of xylosides of taxols A,B,C (taxol analogues A,B,C), 7-xylosyl-10-deacetyl taxol A,B,C of the formula (1), where R represents $C_6H_5$ (taxol analogue A or xyloside A), or $CH_3C=CHCH_3$ (taxol analogue B or xyloside B), or $C_5H_{11}$ (taxol analogue C or xyloside C) into important precursors 10-deacetyl taxols A,B,C (10-DAT A,B,C) of the formula (2) where R represents $C_6H_5$ (10-deacetyl taxol A), or $CH_3C=CHCH_3$ (10-deacetyl taxol B) or $C_5H_{11}$ (10-deacetyl taxol C). 10-deacetyl taxols A,B,C (10-DAT A,B,C) of the formula (2) where R represents $C_6H_5$ (10-deacetyl taxol A), or $CH_3C=CHCH_3$ (10-deacetyl taxol B) or $C_5H_{11}$ (10-deacetyl taxol C). In our prior art process the analogues 7-xylosyl-10-deacetyl taxols A,B,C were isolated from the stem bark of *Taxus wallichiana* with an improved yield, converting the isolated analogues 7-xylosyl-10-deacetyl taxols A,B,C into the intermediates 10-deacetyl taxols A,B,C and finally converting the intermediates 10-deacetyl taxols A,B,C into taxols A,B,C [S. K. Chattopadhyay et al European Patent application No. 97306905.7-1521, Dec. 2, 1997]. In our currently developed improved process, the process of our prior art involving the conversion of the taxol analogues 7-xylosyl-10-deacetyl taxols A,B,C into the intermediates 10-deacetyl taxols A,B,C has been improved.

The starting material 7-xylosyl-10-deacetyl taxols A,B,C for the above conversion reaction, could be isolated from the stem bark of *Taxus wallichiana* by the application of our patented process [A process for the production of taxol. S. K. Chattopadhyay, R. P. Sharma, Sushil Kumar and K. P. Madhusudanan, European patent Application No. 97306905.7-1521, Dec. 2, 1997]. The improved process developed comprises dissolving the isolated analogues 7-xylosyl-10deacetyl taxol A or B or C in a polar solvent, reacting the resultant solution with periodate for 20–40 hours at 20–40° C. to cleave the diol system of the xyloside into dialdehyde, treating the generated di aldehyde in a mixture of polar solvent organic acid mixture with salts of amine at 0–40° C. for 12–18 hours and isolating the product by chromatography to 10-deacetyl taxols A or B or C.

A comparison between our currently developed improved process and prior art process reveals that—(a) the starting material 7-xylosyl-10-deacetyl taxols A,B,C are common in both cases, (b) 7-xylosyl-10-deacetyl taxols A,B,C are oxidized by periodates in a polar solvent into dialdehydes in both the processes and finally, (c) the yields of the intermediates 10-deacetyl taxols A,B,C are comparable in both the processes; However, in our prior art process, the dialdehyde was first reduced with borohydrides and the reduced product was treated with mineral acids into the intermediates 10-deacetyl taxols; In contrast, in our currently developed improved process, the dialdehydes was directly converted into the intermediates 10-deacetyl taxols A,B,C with amine salts.

According to one embodiment of the invention, the polar solvent used in dissolving the taxol analogues 7-xylosyl-10-deacetyl taxols A,B,C and in the mixture of polar solvent organic acid mixture used as a medium in the reaction of amine salts may be selected from methanol ethanol, propanol, isopropanol, butanol, isobutanol.

According to another embodiment of the invention, suitable periodates use din cleaving the diol system of the xyloside may be selected from sodium periodate, potassium periodate, periodic acid, paraperiodic acid.

According to another embodiment of the present invention, the organic acid used in the mixture of polar solvent for the reaction medium or amine salts may be selected from formic acid, propionic acid, oxalic acid, acetic acid, citric acid.

According to another embodiment of the invention, the amine salts may be selected from dimethyl hydrazine hydrochloride, diethyl hydrazine sulphate, methyl phenyl hydrazine hydro chloride, phenyl hydrazine hydrochloride, methyl hydrazine hydrochloride.

According to another embodiment of the present invention, the adsorbent used in the chromatography for isolating 10-deacetyl taxols A,B,C may be selected from silica gel, florosil, alumina.

The invention is described in details in the examples given below which are provided to illustrate the invention and therefore should not be construed to limit the scope of the invention.

EXAMPLE 1

Production of 10-deacetyl taxol A (10-DAT,A)

To a small reaction flask was added the analogue 7-xylosyl-10-deacetyl taxol A (200 mg) in ethanol (30 ml); Sodium periodate (450 mg in 4 ml water) was added to the resulting solution and the reaction mixture was stirred for 20–40 hours at 20–40° C. The reaction mixture was diluted with water and extracted with ethyl acetate (2×50 ml). The ethyl acetate phase was washed with water, dried over anhydrous sodium sulphate and concentrated in vacuo to a residue. The residue was dissolved in a mixture of ethanol-acetic acid and was treated with dimethyl hydrazine hydrochloride (400 mg) for 12–18 hours at 0–40° C. with stirring; The reaction mixture was diluted with water and extracted with chloroform (2×50 ml). The chloroform layer was washed with water (2×50 ml), dried over anhydrous sodium sulphate and concentrated in vacuo to give a residue of 10-DAT, A. It was purified by column chromatography over silica gel eluted first with chloroform—methanol (98;2) and then with chloroform—methanol (95:5). The eluant of the latter fraction was concentrated to give a white amorphous residue of 10-DAT,A (140 mg) which was found to be identical with an authentic sample in all respects [19-hydroxybaccatin III, 10-deacetyl cephals mannine and 10-deacetyl taxol: New antitumor taxanes from *Taxus wallichiana*.

J. L. Mclaughlin, R. W. Miller, R. G. Powell and C. R. Smith, Jr. *Journal of Natural Products* 44, 312–319 (1981)].

EXAMPLE 2

Production of 10-deacetyl taxols (10-DAT,B)

To a small reaction flask was added the analogue 7-xylosyl-10-deacetyl taxol B (200 mg) in methanol (30 ml); Sodium periodate (450 mg in 4 ml water) was added to the resulting solution and the reaction mixture was stirred for 20–40 hours at 20–40° C. The reaction mixture was diluted with water and extracted with ethyl acetate (2×50 ml). The ethyl acetate phase was washed with water, dried over anhydrous sodium sulphate and concentrated in vacuo to a residue. The residue was dissolved in a mixture of ethanol-formic acid and was treated with methyl phenyl hydraxine hydrochloride (300 mg) for 12–18 hours at 0–40° C. with stirring. The reaction mixture was diluted with water and extracted with chloroform (2×50 ml). The chloroform layer was washed with water (2×50 ml), dried over anhydrous sodium sulphate and concentrated in vacuo to give a residue of 10-DAT, B. It was purified by column chromatography over florosil eluted first with chloroform-methanol (98:2) and then with chloroform-methanol (95:5). The eluant of the latter fraction was concentrated to give a white amorphous residue of 10-DAT, B (141 mg) which was found to be identical with an authentic sample in all respect [R. W. Miller et al J. Org. Chem. 46, 1469–1474 (1981)].

EXAMPLE 3

Production of 10-deacetyl taxol C

To a small reaction flask was added the analogue 7-xylosyl-10-deacetyl taxol C (200 mg) in ethanol (300 ml); Sodium periodate (450 mg in 4 ml water) was added to the resulting solution and the reaction mixture was stirred for 20–40 hours at 20–40° C. The reaction mixture was diluted with water and extracted with ethyl acetate (2×50 ml). The ethyl acetate phase was washed with water, dried over anhydrous sodium sulphate and concentrated in vacuo to a residue. The residue was dissolved in a mixture of methanol—acetic acid and was treated with diethyl hydrozine sulphate (500 mg) for 12–18 hours at 0–40° C. with stirring. The reaction mixture was diluted with water and extracted with chloroform (2×50 ml). The chloroform layer was washed with water (2×50 ml), dried over anhydrous sodium sulphate and concentrated in vacuo to give a residue of 10-DAT, C.

It was purified by column chromatography over silica gel eluted first with chloroform-methanol (98:2) and then with chloroform-methanol (95:5). The eluant of the latter fraction was concentrated to give a white amorphous residue of 10-DAT,C (141 mg) which was found to be identical with an authentic sample in all respects [W. Ma et al *J. Nat. Prod.* 57,116–122 (1994)].

Advantages

1) Compared to the previous art, diol of the xyloside system of the analogues 7-xylosyl-10deacetyl taxols A,B,C was cleaved under non-acidic condition; No acid is used in the periodate oxidation step.

2) Compared to the previous art, no heating is used to accomplish the degradation of the dialdehyde into 10-deacetyl taxols A,B,C.

3) All the reagents that are used for this improved process are very cheap and thus the process will be cost effective on a commercial scale.

4) Although the previous process developed by us for conversion of the analogues 7-xylosyl-10-deacetyl taxols A,B,C into 10-deacetyl taxols A,B,C is comparable in yields to our current improved process, the latter is more simpler and cost effective than the previous one.

5) The yields of 10-deacetyl taxols A,B,C obtained by the process of the present invention has been compared with the corresponding yield reported earlier.

| Source | 10-deacetyl taxol A | 10-deacetyl taxol B | 10-deacetyl taxol C |
|---|---|---|---|
| Mixture of roots, stem and needles of Taxus wallichiana | 0.0021% | 0.0038% | Not isolated |
| Callus culture of Taxus baccata | Not isolated | Not isolated | 0.0001% |
| Previous Art (Rao's process) | 0.04% | Could not be calculated on reported data. | Not mentioned |
| Present Process | 0.35% | 0.014% | 0.005% |

What is claimed is:

1. An improved process for the production of important taxol analogues 10-deacetyl taxol A,B and C of the formula (2)

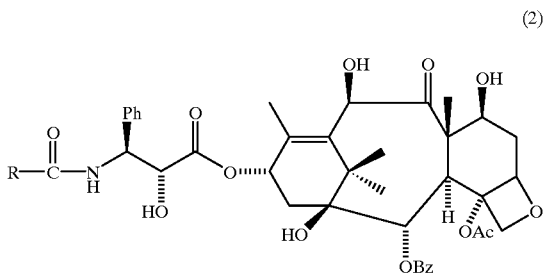

(2)

R=$C_6H_5$(10 deacetyl taxol A)
=$CH_3C$=$CHCH_3$ (10-deacetyl taxol B)
=$C_5H_{11}$ (10-deacetyl taxol C)

where R represents $C_6H_5$ (10-deacetyl taxol A) or, $CH_3C$=$CHCH_3$ (10-deacetyl taxol B) or, $C_5H_{11}$ (10-deacetyl taxol C) which comprises (a) dissolving the taxol analogues 7-xylosyl-10-deacetyl taxol A,B,C of the formula (1)

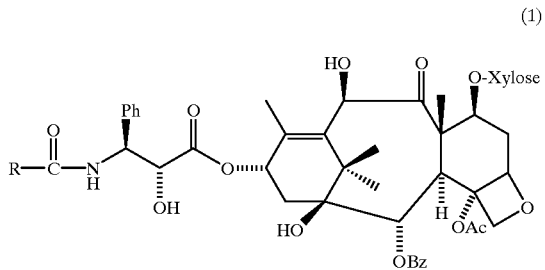

(1)

R=$C_6H_5$ (10 deacetyl taxol A)
=$CH_3C$=$CHCH_3$ (10-deacetyl taxol B)
=$C_5H_{11}$ (10-deacetyl taxol C)

where R represents $C_6H_5$ (taxol analogue A or xyloside A), or $CH_3C$=$CHCH_3$ (taxol analogue B or xyloside B) or $C_5H_{11}$ (taxol analogue C or xyloside C) in a polar solvent (b) reacting the resultant solution with periodate for 20–40 hours at 20–40° C. to cleave the diol system of the xyloside into dialdehyde, (c) treating the generated dialdehyde in a mixture of polar solvent-organic acid mixture with salts of amines at 0–40° C. for 12–18 hours and (d) isolating the 10-deacetyl taxol A,B,C by chromatography.

2. A process as claimed in claim 1 wherein the polar solvents used in dissolving the taxol analogues 7-xylosyl-10-deacetyl taxols A,B,C and in the mixture of polar solvent organic acid mixture used as a medium in the reaction of amine salts are selected from methanol, ethanol, proponol, isopropanol, butanol, isobutanol.

3. A process as claimed in claim 1 wherein the periodates used in cleaving the diol system of the xyloside are selected from sodium periodate, potassium periodate, periodic acid, paraperiodic acid.

4. A process as claimed in claim 1 wherein the organic acid used in the mixture of polar solvent for the reaction medium of amine salts are selected from formic acid, propionic acid, oxalic acid, acetic acid, citric acid.

5. A process as claimed in claim 1 wherein the salts of amines are hydrazine/hydroxyl amine salts and are selected from dimethyl hydrazine hydrochloride, diethyl hydrazine sulphate, methyl phenyl hydrazine hydrochloride, phenyl hydrazine hydrochloride, methyl hydrazine hydrocloride.

6. A process as claimed in claim 1 wherein the absorbent used in the chromatography for purifying 10-deacetyl taxols, A,B,C are selected form silica gel, florosil, alumina.

7. A process as claimed in claim 1 wherein in step (b) said reaction with periodate is effected in the absence of an acid.

8. A process as claimed in claim 1 wherein step (b) is effected in a reaction environment consisting essentially of a taxol analogue selected from the group consisting of taxol xyloside A, taxol xyloside B and taxol xyloside C, a polar solvent selected from the group consisting of methanol, ethanol, propanol, isopropanol, butanol and isobutanol and a periodate selected from the group consisting of sodium periodate, potassium periodate selected from the group consisting of sodium periodate, potassium periodate, periodic acid and paraperiodic acid.

9. A process as claimed in claim 8 wherein the product obtained is reacted with an amine salt selected from the group consisting of dimethyl hydrazine hydrochloride, diethyl hydrazine sulphate, methyl phenyl hydrazine hydrochloride, phenyl hydrazine hydrochloride and methyl hydrazine hydrochloride.

10. A process as claimed in claim 9 wherein said reaction with an amine salt is carried out in the presence of a solvent selected from the group consisting of formic acid, propionic acid, oxalic acid, acetic acid and citric acid.

11. A process as claimed in claim 9 wherein said reaction with an amine salt is carried out at a temperature of from 0–40° C.

* * * * *